US008529807B2

(12) United States Patent
Neuland et al.

(10) Patent No.: US 8,529,807 B2
(45) Date of Patent: Sep. 10, 2013

(54) METHOD FOR NEUTRALIZING OR RECYCLING CARRIER MATERIALS FOR FILM-LIKE COATINGS

(75) Inventors: Detlev Neuland, Wangen-Neuravensburg (DE); Wolfgang Schaefer, Madison, NJ (US); Peter Schwarz, Koenigswinter (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 946 days.

(21) Appl. No.: 10/501,247

(22) PCT Filed: Jan. 14, 2003

(86) PCT No.: PCT/EP03/00252
§ 371 (c)(1), (2), (4) Date: Jul. 12, 2004

(87) PCT Pub. No.: WO03/059542
PCT Pub. Date: Jul. 24, 2003

(65) Prior Publication Data

US 2004/0258737 A1 Dec. 23, 2004

Related U.S. Application Data

(60) Provisional application No. 60/349,782, filed on Jan. 17, 2002.

(51) Int. Cl.
*A61F 13/00* (2006.01)
*B28B 7/04* (2006.01)
*B29B 17/00* (2006.01)
*B29D 7/00* (2006.01)
*D01F 13/00* (2006.01)

(52) U.S. Cl.
USPC ............. 264/39; 264/37.1; 264/212; 424/443

(58) Field of Classification Search
None
See application file for complete search history.

(56) References Cited

U.S. PATENT DOCUMENTS

| | | | | | |
|---|---|---|---|---|---|
| 2,486,258 | A | * | 10/1949 | Chavannes | 156/237 |
| 2,575,046 | A | * | 11/1951 | Chavannes et al. | 156/280 |
| 4,079,106 | A | * | 3/1978 | Goldsworthy et al. | 264/46.2 |
| 4,455,143 | A | * | 6/1984 | Theeuwes et al. | 604/892.1 |
| 4,517,173 | A | * | 5/1985 | Kizawa et al. | 424/435 |
| 4,562,020 | A | * | 12/1985 | Hijiya et al. | 264/39 |
| 4,569,837 | A | * | 2/1986 | Suzuki et al. | 514/772.2 |
| 4,592,753 | A | * | 6/1986 | Panoz | 424/449 |
| 4,622,761 | A | * | 11/1986 | Barth | 34/86 |
| 4,788,063 | A | * | 11/1988 | Fisher et al. | 424/449 |
| 4,871,559 | A | * | 10/1989 | Dunn et al. | 426/248 |
| 4,925,670 | A | | 5/1990 | Schmidt | 424/443 |
| 4,978,836 | A | * | 12/1990 | Dieudonne et al. | 219/388 |
| 5,064,654 | A | * | 11/1991 | Berner et al. | 424/448 |
| 5,112,220 | A | * | 5/1992 | Wimberger et al. | 432/8 |
| 5,629,003 | A | | 5/1997 | Horstmann et al. | 424/401 |
| 5,804,357 | A | * | 9/1998 | Yamanouchi et al. | 430/438 |
| 5,948,430 | A | | 9/1999 | Zerbe et al. | 424/435 |
| 6,153,298 | A | * | 11/2000 | Joson | 428/349 |
| 6,183,775 | B1 | * | 2/2001 | Ventouras | 424/465 |
| 2001/0006677 | A1 | * | 7/2001 | McGinity et al. | 424/449 |
| 2003/0228196 | A1 | * | 12/2003 | Satchwell et al. | 405/128.5 |
| 2005/0287195 | A1 | * | 12/2005 | Solomon et al. | 424/449 |

FOREIGN PATENT DOCUMENTS

| | | | |
|---|---|---|---|
| EP | 0 219 762 | A1 | 4/1987 |
| EP | 0 796625 | A1 | 9/1997 |

OTHER PUBLICATIONS http://www.teflon.com/NASApp/Teflon/TeflonPageServlet?pageId=/consumer/na/eng/housewares/cookware/cookware/nonStick/cookwareCare/cookware_care.html (copyright 1995).*
Bittner et al. Journal of Controlled Release 1999 59:23-32.*
Lerdkanchanaporn et al. Thermochimica Acta 2000 357-358:71-78.*
Lerdkanchanaporn et al. Journal of Thermal Analysis 1887 49:879-8.*
Charara et al. Journal of Food Science 1992 57:963-968.*
Peacock Handbook of Polyethylene Marcel Dekker Inc:New York 2000 p. 185-187.*

* cited by examiner

*Primary Examiner* — Robert A Wax
*Assistant Examiner* — Caralynne Helm
(74) *Attorney, Agent, or Firm* — ProPat, L.L.C.

(57) ABSTRACT

The present invention relates to methods by which to produce sheet-like, wafer-like or film-like forms of drugs, confectionary, other food, cosmetics and the like for oral application or intake. The present invention is more particularly directed to the thermal treatment of carrier materials used in the production of such sheet-like, wafer-like or film-like forms. The thermal treatment removes contaminating or undesired substances from the carrier material.

9 Claims, No Drawings

METHOD FOR NEUTRALIZING OR RECYCLING CARRIER MATERIALS FOR FILM-LIKE COATINGS

CROSS-REFERENCE TO RELATED APPLICATIONS

This application is being filed under Rule 1.371 as a National Stage Application of International Application No. PCT/EP03/00252 filed Jan. 14, 2003, which claims priority to U.S. Provisional Application No. 60/349,782, filed Jan. 17, 2002. Both International Application No. PCT/EP03/00252 and U.S. Provisional Application No. 60/349,782 are hereby incorporated by reference herein in their entirety.

FIELD OF THE INVENTION

This invention relates to methods by which to produce drugs, confectionary, other food, cosmetics and the like for oral application or intake. This invention more specifically relates to methods by which to produce sheet-like, wafer-like or film-like forms of drugs, confectionary, other food, cosmetics and the like for oral application or intake.

BACKGROUND OF THE INVENTION

It is well known in the art to manufacture and use sheet-like, wafer-like or film-like forms of administration of drugs, confectionary, other food, cosmetics and the like for oral application or intake; e.g. U.S. Pat. Nos. 5,629,003, 5,948,430, 4,925,670 and the references cited in these patent specifications. The main advantage in using the above forms of administration, especially as regards oral intake of drugs or cosmetic active ingredients, is the avoidance of unnecessary inactive ingredients which may be contained in a tablet or capsule in an amount of up to 99% relative to the tablet weight.

Various production processes are known for the manufacture of sheet-like, wafer-like or film-like forms of administration. For example, it is stated in U.S. Pat. No. 4,925,670 that the application of the active agent-containing coating, which in many cases is an aqueous coating composition, to the carrier material preferably takes place with the aid of a smooth roll coating process. Depending on its chemical nature the coating substance may be heated e.g. to approximately 40 to 100° C. and it is applied in a thin coating using a closed application system on a roller. With delayed synchronism in specific selectable ratios the material can be transferred to a parallel roller whereby, if necessary, a reduction of the coating thickness can take place, so that simultaneously the tolerances during application are reduced by these factors.

The coating of the carrier material takes place synchronously by means of a further roller system. On adapting the active agent coating material to the release value of the carrier material, there may be no need to add an adhesive. However, optionally suitable adhesives can be added.

When applying several coating layers, the layers are successively applied with each coating optionally directed to a drying station. This can, for example, comprise a thermostatically controlled pair of rollers and a drying tunnel controllable in sectional form. After the drying process, which can take place in different separate steps at different pre-defined temperatures, the coated material, i.e. carrier material carrying the optionally various layers of coatings, is wound on to reels.

In general, it can be said that the above mentioned sheet-like, wafer-like or film-like forms of administration are manufactured by producing thin sheets of an active-ingredient film which are applied to a carrier or substrate material by casting the film material onto the substrate material or coating a substrate material with the active agent-containing coating and winding the product on to reels. Usually in an additional step the active-ingredient containing coating is peeled off the carrier material and cut into pieces of a shape and size suitable for the intended use and the carrier material is again wound on to reels.

All these different process steps are usually carried out in a fully automated and integrated production or coating line comprising reels or roller systems, means for applying the coating to the carrier material (coating-head), e.g. a knife-over-roll coating head, and a drying tunnel with zones of different temperatures. Such coating lines are known in the art (e.g. EP-A-0 219 762).

Various materials can be used as the carrier, e.g. papers weighing approximately 80 to 120 g/m$^2$, plastic film or sheets comprising polyethylene, polyvinylchloride, polyvinylidene chlroide, polyesters or other polymers or thin metal foils, for exmple, those made from aluminum. Usually preference is given to siliconized papers which are commercially available and which have largely replaced wax or paraffin-coated release papers. Furthermore, also composite materials composed of paper, polymers and/or thin metal foils, preferably aluminum, are also advantageously used in producing the forms of administration.

As outlined above for producing these forms of administration the carrier material which is wound on to reels is fed to the production line where it is coated with the active ingredient containing material. The resulting product is dried in a drying tunnel and wound on to reels. The active-ingredient containing coating is peeled off the carrier for further processing the resulting film and the carrier material is again wound on to reels.

However, during the above production process the active-ingredient and additionally used adjuvants and other components of the coating used e.g in a pharmaceutical preparation will partly, through diffusion, penetrate into the carrier material. The carrier material will be contaminated by these substances up to the respective degrees of saturation. The same holds true with regard to cosmetically active agents and their respective components which may include e.g. breath freshening compounds like menthol other flavors or fragrances commonly used for oral hygiene.

Therefore, when applying the coating composition to the carrier material the above penetration of substances and the contamination of the carrier material has to be considered in order to arrive at a final active ingredient containing film which has the desired pre-determined composition resulting in the desired properties. This is especially important when it comes to sheet-like, wafer-like or film-like forms of administration for drugs.

Thus, once the active ingredient containing film has been peeled off the carrier material for further processing the contaminated carrier wound on to reels cannot be used again for coating purposes since it is already loaded to a non-specified degree with the substances as described above. If the carrier would be coated with the same coating material a second time the active ingredients, adjuvants, flavors etc. would to a different extent penetrate into the pre-loaded carrier as compared to the first coating procedure and, thus, the composition of the resulting active ingredient containing coating or film could change significantly. Especially this is not tolerable as regards film-like administration forms of drugs.

The same problem arises if one would apply to the pre-loaded carrier material a coating of different composition. Additionally this coating could be contaminated by substances penetrating from the pre-loaded carrier into the new coating.

Therefore, usually any further use of such carrier material is almost not possible. Since the costs for carrier materials contribute largely to the overall production costs, and also from an environmental perspective in terms of removing of waste, it would be highly desirable to neutralize, recycle or recondition these carrier materials for further use.

SUMMARY OF THE INVENTION

The present invention provides a method for neutralizing, recycling or reconditioning of carrier materials used in the manufacture of sheet-like or film-like forms of administration of drugs, confectionary, other food, cosmetics and the like for further use.

DETAILED DESCRIPTION OF THE INVENTION

The present invention provides a method for removing substances, e.g. active ingredients, adjuvants, flavors etc., from carrier materials which have penetrated these carrier materials while producing the above mentioned forms of administration. As stated above the contaminated carrier materials are usually wound on to reels once the film coating as been peeled off. It has been found that by an appropriate thermal treatment of these carrier materials the contaminants, i.e. the substances which penetrated the material during the production process, can be removed there from resulting in a so-called neutralized carrier material being essentially free of those contaminants, which then can be used as carriers in further coating processes.

The period of the thermal follow-up treatment and the temperatures to be applied vary depending mainly from the following features:

1. concentration of the contaminating substances in the carrier material (degree of contamination)
2. type of substances (chemical and physical characteristics) and type of coating compositions (usually aqueous compositions)
3. type of carrier material (e.g. paper, polymers, composite materials from paper, polymers and/or thin metal foils)

However, time and temperature can be easily assessed through simple experiments using conventional means and methods of chemical analysis.

In most cases good results in removing the contaminating substances from conventional carrier materials are achieved by treating these materials at approx. 80° C. for a period of approx. 0.5 to 6 minutes.

This process can for example be performed in an automated manner by unwinding the contaminated carrier from a reel and feeding it to a thermal treatment zone, like the drying tunnel of a coating line, where the material is heated, e.g. by infra red heating, to the appropriate temperature. The time of treatment can be controlled via the speed at which the material is passing the thermal treatment zone. The contaminating substances will evaporate and can be feed to a thermal after-burning using a controlled air circulation. Having passed this heating zone the carrier material, if necessary, can be cooled down by using a material compensator and is then feed again to the coating-head of a coating line for the next coating step. Thus, the removal of the undesired substances contaminating the carrier material can be carried out by using a slightly modified conventional coating line.

The invention claimed is:

1. A method for removing contaminating substances from a polymer carrier material comprising a) heating an active-ingredient-containing drug, food or cosmetic-containing coating composition to approximately 40 to 100° C., b) coating the heated active-ingredient-containing drug, food or cosmetic coating composition onto a neutralized polymer carrier material via synchronized rollers, flavor and/or fragrance within said coating composition diffusing into and thereby contaminating said polymer carrier material with flavor and/or fragrance, wherein the polymer carrier material is supplied on a reel, c) drying the coated polymer carrier material to form an active-ingredient-containing drug, food or cosmetic film, d) peeling the dried active-ingredient-containing film off the contaminated polymer carrier material and e) subjecting the contaminated polymer carrier material to a thermal treatment which comprises i) passing said contaminated polymer carrier material through a thermal treatment zone whose temperature is approximately 80° C. and for a period of time of approximately 0.5 to 6 minutes that is sufficient to remove the flavor and/or fragrance from the polymer carrier material to form a neutralized polymer carrier material, and ii) feeding the removed contaminating substances to a thermal after-burner using controlled air circulation, and f) providing the neutralized polymer carrier material to said coating step.

2. A method for removing contaminating substances from a paper carrier material comprising a) heating an active-ingredient-containing drug, food or cosmetic aqueous coating composition to approximately 40 to 100° C., b) coating the heated active-ingredient-containing drug, food or cosmetic coating onto a paper carrier material via synchronized rollers, active ingredients, adjuvants, flavors, or fragrances within said aqueous coating composition diffusing into and thereby contaminating said paper carrier material, wherein said paper carrier material is not a composite with metal foil or another polymer, c) drying the coated paper carrier material to form an active-ingredient-containing drug, food or cosmetic film, d) peeling the dried active-ingredient-containing film off the contaminated paper carrier material and e) subjecting the contaminated paper carrier material to a thermal treatment comprising i) passing said contaminated paper carrier material through a thermal treatment zone at a temperature and during a period of time sufficient to remove active ingredients, adjuvants, flavors, or fragrances from the paper carrier material and ii) feeding the removed active ingredients, adjuvants, flavors, or fragrances to a thermal after-burning using controlled air circulation.

3. A method for removing contaminating substances from a polymer carrier material comprising a) heating an active-ingredient-containing drug, food or cosmetic-containing coating composition to approximately 40 to 100° C., b) coating the heated active-ingredient-containing drug, food or cosmetic coating onto a polymer carrier material via synchronized rollers, flavors and/or fragrances within said coating composition diffusing into and thereby contaminating said polymer carrier material, c) drying the coated polymer carrier material to form a active-ingredient-containing drug, food or cosmetic film, d) peeling the dried film off the contaminated polymer carrier material and e) subjecting the contaminated polymer carrier material to a thermal treatment comprising i) passing said contaminated polymer carrier material through a thermal treatment zone at a temperature and for a period of time sufficient to remove the contaminating flavors and/or fragrances from the polymer carrier material and ii) feeding the removed flavors and/or fragrances to a thermal after-burner using controlled air circulation.

4. A method according to claim 1, wherein said thermal treatment is imparted in a drying tunnel.

5. A method according to claim 1, wherein said thermal treatment consists of an infra red heat treatment.

6. A method according to claim 2, further comprising taking the thermally treated paper carrier material up on a reel.

7. A method according to claim 3, further comprising taking the thermally treated polymer carrier material up on a reel.

8. A method according to claim 1, wherein the polymer carrier material is polyethylene, polyvinylchloride, polyvinylidenchloride or polyester.

9. A method for removing contaminating substances from a paper carrier material comprising a) heating an active-ingredient-containing drug, food or cosmetic-containing coating composition to approximately 40 to 100° C., b) coating the heated active-ingredient-containing drug, food or cosmetic coating composition onto a neutralized paper carrier material via synchronized rollers, flavors, fragrances, adjuvants or active-ingredients within said coating contaminating said paper carrier material, wherein said paper carrier material is not a composite with metal foil or another polymer, c) drying the coated paper carrier material to form an active-ingredient-containing drug, food or cosmetic film, d) peeling the dried active-ingredient-containing film off the contaminated paper carrier material and e) subjecting the contaminated paper carrier material to a thermal treatment which comprises i) passing said contaminated paper carrier material through a thermal treatment zone whose temperature is approximately 80° C. and for a period of time of approximately 0.5 to 6 minutes that is sufficient to remove the flavors, fragrances, adjuvants, or active ingredients from the paper carrier material to form neutralized paper carrier material, and ii) feeding the removed flavors, fragrances, adjuvants, or active ingredients to a thermal after-burner using controlled air circulation, and providing the neutralized paper carrier material to said coating step.

* * * * *